(12) United States Patent
Hansen et al.

(10) Patent No.: US 9,501,949 B2
(45) Date of Patent: Nov. 22, 2016

(54) METHOD AND SYSTEM FOR SELF-MANAGEMENT OF A DISEASE

(75) Inventors: Jon Ulrich Hansen, Herlev (DK); Leif Engmann Kristensen, Frederiksberg (DK); Jette Randlov, Vaerlose (DK); Knud Poulsen, Copenhagen NV (DK); Radisch Ulrik Detlef Poulsen, Hillerod (DK); Jens Ulrik Poulsen, Virum (DK); Jorgen Slot Smedegaard, Vaerlose (DK); Hans Henrik Thodberg, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 2907 days.

(21) Appl. No.: 11/664,561

(22) PCT Filed: Oct. 6, 2005

(86) PCT No.: PCT/EP2005/055064
§ 371 (c)(1),
(2), (4) Date: May 1, 2008

(87) PCT Pub. No.: WO2006/037802
PCT Pub. Date: Apr. 13, 2006

(65) Prior Publication Data
US 2009/0036828 A1 Feb. 5, 2009

Related U.S. Application Data (60) Provisional application No. 60/621,184, filed on Oct. 22, 2004, provisional application No. 60/641,516, filed on Jan. 5, 2005.

(30) Foreign Application Priority Data

Oct. 7, 2004 (DK) .................................. 2004-01537
Dec. 22, 2004 (DK) .................................. 2004-01981

(51) Int. Cl.
*A61M 5/00* (2006.01)
*G09B 19/00* (2006.01)
*G06F 19/00* (2011.01)

(52) U.S. Cl.
CPC ........... *G09B 19/00* (2013.01); *G06F 19/3406* (2013.01); *G06F 19/363* (2013.01)

(58) Field of Classification Search
USPC .......................................................... 600/365
See application file for complete search history.

(56) References Cited

U.S. PATENT DOCUMENTS

| | | | |
|---|---|---|---|
| 5,672,154 A | 9/1997 | Sillen et al. |
| 6,075,755 A | 6/2000 | Zarchan |
| 6,425,863 B1 | 7/2002 | Werner et al. |
| 6,650,951 B1 | 11/2003 | Jones et al. |
| 6,656,114 B1 | 12/2003 | Poulsen et al. |
| 2002/0097156 A1 | 7/2002 | Broas |
| 2003/0028089 A1 | 2/2003 | Galley et al. |
| 2004/0034288 A1 | 2/2004 | Hennessy et al. |
| 2004/0178112 A1 | 9/2004 | Snyder |

FOREIGN PATENT DOCUMENTS

| | | |
|---|---|---|
| CA | 2445598 A1 | 11/2002 |
| EP | 290683 A2 | 11/1988 |
| EP | 483595 A2 | 5/1992 |
| EP | 0834825 A1 | 4/1998 |
| EP | 1197907 A2 | 4/2002 |
| EP | 1281351 A2 | 2/2003 |
| JP | 2003-079723 A | 3/2003 |
| JP | 2003-167961 A | 6/2003 |
| JP | 4348747 B2 | 10/2009 |
| RU | 2221594 C2 | 1/2004 |
| WO | WO 99/38052 | 7/1999 |
| WO | 99/49777 A1 | 10/1999 |
| WO | 00/18293 A1 | 4/2000 |
| WO | 00/18449 A2 | 4/2000 |
| WO | WO 00/32088 | 6/2000 |
| WO | 00/49549 A1 | 8/2000 |
| WO | 01/72208 A2 | 10/2001 |
| WO | 01/87402 A1 | 11/2001 |
| WO | 02/087506 A2 | 11/2002 |
| WO | 02/089663 A1 | 11/2002 |
| WO | WO 03/005891 A1 | 1/2003 |
| WO | 03/015629 A1 | 2/2003 |
| WO | WO 03/015838 A3 | 2/2003 |
| WO | WO 03/015838 R6 | 2/2003 |
| WO | 03/047426 | 6/2003 |
| WO | WO 04/001539 A2 | 12/2003 |
| WO | 2004/023972 A2 | 3/2004 |

*Primary Examiner* — Karen Canella
(74) *Attorney, Agent, or Firm* — Wesley Nicolas (57) ABSTRACT

The present specification discloses a method, system and program product that can be used for self-management of any chronic disease. The invention involves the use of a device to enter patient's disease related data. Based on this data patient's habits are detected and presented in a graphical format. The user also has the option of setting up a reminder based on the detected habits.

14 Claims, 6 Drawing Sheets

METHOD AND SYSTEM FOR SELF-MANAGEMENT OF A DISEASE

CROSS-REFERENCE TO RELATED APPLICATIONS

This application is a 35 U.S.C. §371 national stage application of International Patent Application PCT/EP2005/055064 (published as WO 2006/037802), filed Oct. 6, 2005, which claimed priority of Danish Patent Applications PA 2004 01537, filed Oct. 7, 2004 and PA 2004 01981 filed Dec. 22, 2004; this application further claims priority under 35 U.S.C. §119 of U.S. Provisional Applications 60/621,184, filed Oct. 22, 2004 and 60/641,516 filed Jan. 5, 2005.

FIELD OF THE INVENTION

The present invention relates to the field of self-care of a disease using electronic data analysis devices.

BACKGROUND OF THE INVENTION

Chronicle diseases and other physiological conditions such as diabetes, asthma or the like, that require effective therapeutic care over long periods of time have become a widespread phenomenon. Typically, such diseases require medication and/or a control of the patient's lifestyle.

Diabetes is one such chronic condition of the human body in which lack of insulin raises the blood sugar levels which in turn has harmful effects that sometimes may even endanger the patient's life. A diabetic has to be very careful about the level of blood sugar in his/her body and therefore has to constantly monitor the activities that are likely to have an impact on the same. To keep the blood sugar level in check, a diabetic has to sometimes take artificial insulin. As of now this is generally done by way of insulin injections. These injections have to be administered after considering the patient's present condition as well as carefully predicting the near future state. To this end, various blood sugar measurement devices such as strips and meters are available in the market. For the ease of operation by the user as well as for portability, the measurement devices have also been combined with insulin administration devices. This way the patient can carry one device that would not only measure his/her disease related parameters but would also assist him/her in administering his/her medicine.

With the advancement in technology, these devices have become even more sophisticated and now incorporate additional functionality such as recording the patient's disease related data and other useful information. Some of these devices also have communication means that connect them to other computing devices to form a network. The patient, the patient's doctor and other people can then use the information present on these devices in various ways such as for analysis. International Publication Nos. WO 00/32088, WO 03/005891 and WO 03/015838 all describe such medical devices, networks and method of their operation along with some of the possibilities in the domain. These publications are incorporated herein in entity by way of reference.

US Publication No. US 2003/0028089 discloses a system for managing diabetes that allows the patient to enter his data and in turn recommends the future insulin intake for the patient. However, it remains up to the patient to follow the recommended actions, and there remains a need for a method that assists a user in following a prescribed treatment plan.

US publication no. U.S. Pat. No. 6,650,951 discloses an insulin pump that issues a warning if the user forgets to initiate a bolus within a predetermined period after a meal time. Even though the issued warnings help a user to remember a forgotten bolus, the above prior art system forces a user into a rather strict schedule of meals and does not address the problem of providing a self-management system that is flexible with respect to individual user's lifestyles.

SUMMARY OF THE INVENTION

According to a first aspect, the above and other problems are solved by a method of assisting a user in the self-management of a physiological condition, the method comprising
  obtaining data about occurrences of at least a first type of user actions;
  detecting a user habit from the obtained data; and
  generating a reminder data item from the detected user habit.

Hence, a method is provided by which a patient's behavior and habits are identified and reminders are generated based on the identified habits that remind the patient to follow a consistent lifestyle, thereby improving the treatment and/or control of the patient's disease.

Habits may comprise the typical time of day of certain actions, such as typical meal times, typical times at which the patient measures a physiological parameter such as the blood glucose level, typical times and doses of medication, etc. Accordingly, the user action may be any action that has influence on the physiological condition to be controlled. Examples of such actions include meal intakes, medication, such as insulin delivery, measurements of a physiological parameter such as blood glucose level, physical activity, or the like.

Identifying such habits facilitates the user to follow his/her individual habits in a consistent way, thereby allowing a combination of a tight control of the user's lifestyle while providing a high degree of individual freedom and an increased quality of life. In particular, by providing a method that receives patient related data (such as blood glucose, insulin intake etc.) as an input and analyses the data to identify user habits and behavior, the self-management of the patient can be customized to the individual patient's lifestyle while still providing control over the patient's day-to-day activities so that his diabetes can be efficiently managed. Preferably, detecting a user habit comprises determining a distribution of occurrences of the first type of user actions over a predetermined period of time, such as a modal day.

It is a further advantage that the observance of the patient's habits and the data recording may be performed by the user himself/herself, thereby increasing the user's independence from health care personnel and, thus, increasing the user's quality of life. Furthermore, the monitoring and data recording by the user increases the possibility of constant observance, thereby improving the quality of the recorded data.

When the reminder data item comprises a time interval during which the user action is to be performed, the reminder system may generate a reminder if the user has not performed the corresponding action within the time interval. Hence, on one hand, redundant reminders are avoided if the action has been performed slightly ahead of time but within the time limit. On the other hand it is ensured that a previous occurrence of the user action (e.g. in connection with a previous meal) before the start of the time limit, is not erroneously interpreted as a compliance with the current action. Accordingly, in a preferred embodiment, detecting the user habit/habitual pattern includes detecting a time interval during which said first type of user actions typically occurs.

In one embodiment, the user action comprises delivery of a medicament such as insulin, and detecting the user habit/habitual pattern includes detecting a typical dose interval of the medicament. Consequently, not only the temporal aspects of the user's habits are identified and, thus, subsequently controlled, but also further parameters of the user action. In particular, the correct dose of the delivered medicaments is typically essential for a successful treatment.

In a preferred embodiment detecting the user habit comprises determining a time of day and a dose of each medication intake;

determining respective numbers/counts of medication intakes within a plurality of time intervals and with a dose within a predetermined dose interval to obtain a distribution of medication intakes as function of time of day and of dose; and determining a combination of a time interval and a dose interval as a maximum of said distribution.

It has turned out that the habit detection process described herein provides an efficient and accurate detection of the user's medicament delivery habits. It is a further advantage that both the time and dose habits are detected simultaneously, thereby also capturing any correlations between the two parameters.

Accordingly, in a preferred embodiment, the reminder data item comprises a time constraint and a dose constraint for a medication to be taken by a user; and the method further comprises receiving an indication of a medication event, if any, said indication comprising time and dose information about a medication taken by the user;

issuing a reminder if no indication about at least one medication event complying with both the time constraint and the dose constraint of the reminder data item is received.

Consequently, by providing a medication reminder data item that comprises both a time constraint and a dose constraint for a medication to be taken by a user; and by issuing a reminder if at least one of the constraints is not complied with, the reliability of the reminder system is improved, as not only the correct timing of the medication is supervised but also the correct doses at the different times. Consequently, the efficiency of the therapy is greatly improved.

In another embodiment, the recorded data and/or the identified habits are displayed to the user in a graphical format, thereby allowing a visualization of the detected habits. When generating a reminder data item comprises presenting at least one suggested parameter of the reminder data item to the user, and providing editing means allowing the user to edit the suggested parameter, the user may verify the detected habits and edit/fine tune the corresponding reminders.

It is an advantage of the method and system described herein that the change of detected but undesired user habits is greatly facilitated, thereby supporting the improvement of the user's quality of life and/or health.

In another embodiment, detecting the user habit comprises determining a time of day of each of the occurrences of the first type of user actions;

determining respective numbers/counts of said occurrences within a plurality of time intervals; and determining one of said time intervals as corresponding to a largest number/count of occurrences.

In an alternative embodiment, detecting the user habit comprises determining a time of day of each of the occurrences of the first type of user actions;

generating a predetermined distribution function such as a Gaussian distribution function around each occurrence;

combining the generated distribution functions to obtain a combined distribution functions; and determine a user habit as a maximum of the combined distribution function.

Hence, an efficient and accurate detection of the time of day of predetermined user habits is provided.

Accordingly, in a preferred embodiment, the reminder data item comprises a time interval of a modal day during which a user should take an action of the first type; and the method further comprises receiving an indication when a user action of the first type has occurred;

issuing a reminder if no indication about an occurred user action has been received within said time interval.

According to a second aspect, an improved reliability of the reminders is provided by a method of assisting a user in the self-management of a physiological condition, the method comprising providing a medication reminder data item, the medication reminder data item comprising a time constraint and a dose constraint for a medication to be taken by a user;

receiving an indication of a medication event, if any, said indication comprising time and dose information about a medication taken by the user;

issuing a reminder if no indication about at least one medication event complying with both the time constraint and the dose constraint of the reminder data item is received.

In particular, by providing a medication reminder data item that comprises both a time constraint and a dose constraint for a medication to be taken by a user; and by issuing a reminder if at least one of the constraints is not complied with, the reliability of the reminder system is improved, as not only the correct timing of the medication is supervised but also the correct doses at the different times. Consequently, the efficiency of the therapy is greatly improved.

In a preferred embodiment, the method further comprises obtaining data about occurrences of medication events by the user;

detecting a user habit/habitual pattern from the obtained data; and generating the medication reminder data item from the detected user habit.

Hence, a method is provided by which a patient's behavior and habits are identified and reminders are generated based on the identified habits that remind the patient to follow a consistent lifestyle, thereby improving the treatment and/or control of the patient's disease.

Preferably detecting the user habit/habitual pattern includes detecting a time interval during which said medication events typically occur and detecting a typical dose interval of the medicament for each medication event.

In a preferred embodiment, detecting the user habit comprises
   determining a time of day and a dose of each medication intake;
   determining respective numbers/counts of medication intakes within a plurality of time intervals and with a dose within a predetermined dose interval to obtain a distribution of medication intakes as function of time of day and of dose; and
   determining a combination of a time interval and a dose interval as a maximum of said distribution.

It has turned out that the habit detection process described herein provides an efficient and accurate detection of the user's medicament delivery habits. It is a further advantage that both the time and dose habits are detected simultaneously, thereby also capturing any correlations between the two parameters.

In a preferred embodiment, the medication reminder data item comprises a time interval during which the medication event is to be performed and a dose interval of a dose of a medicament to be applied during said medication event.

Further preferred embodiments are disclosed in the dependant claims.

The present invention relates to different aspects including the methods described above and in the following, corresponding systems, devices, and computer programs, each yielding one or more of the benefits and advantages described in connection with the above-mentioned methods, and each having one or more embodiments corresponding to the embodiments described in connection with the above-mentioned methods.

In particular, according to the first aspect, the invention further relates to a system for assisting a user in the self-management of a physiological condition, the system comprising input means for obtaining data about occurrences of at least a first type if user actions; and processing means adapted to detect a user habit from the obtained data, and to generate a reminder data item from the detected user habit.

According to the second aspect, the invention further relates to a user device for assisting a user in the self-management of a physiological condition, the system comprising
   input means for receiving an indication of a medication event, if any, said indication comprising time and dose information about a medication taken by the user;
   storage means for storing a medication reminder data item, the medication reminder data item comprising a time constraint and a dose constraint for a medication to be taken by a user; and
   processing means adapted to issue a reminder if no indication about at least one medication event complying with both the time constraint and the dose constraint of the reminder data item is received.

The term user device may comprise any electronic equipment, such as a suitably programmed programmable device. Preferably, the device is a portable or wearable device that can be carried by the user, thereby ensuring that the user receives the reminders. For example, the device may be a suitably programmed portable computer, such as a handheld computer, a PDA, or the like. In other embodiments, the device is a suitably programmed mobile telephone, pager, or other mobile communications device.

In some embodiments, the device is a drug administration device, such as an insulin administration device, e.g. an insulin injection device, an insulin inhalator, an insulin pump, an insulin dosing device, an electronically controlled patch, a pulmonial medication device, or the like. Consequently, the reminder system is integrated in a drug administration device, thereby reducing the number of different devices that need to be carried by the user. Furthermore, the drug deliveries by such a combined device may be recorded directly by the device, thereby allowing the recording of the data without the need for an active user input or data transmission from another device. For example, a drug administration device may be capable of storing patient related data such as drug dosage, meal details, blood glucose level etc.

In other embodiments, the device is an insulin measuring device, thereby combining insulin measurements with a reminder system. Consequently, the number of separate devices to be carried by a user is reduced, and the times of day at which the blood glucose is measured may be directly fed into the habit analysis system, thereby reducing the required manual inputs or data transmissions from other devices.

BRIEF DESCRIPTION OF THE DRAWINGS

The above and other aspects will be apparent and elucidated from the embodiments described in the following with reference to the drawing in which:

FIG. 7c shows the strongest three detected habits for fast insulin of FIG. 7a.

DETAILED DESCRIPTION OF THE DRAWINGS

The inventive concept as disclosed herein is useful in any of the diseases or other physiological conditions that require a constant monitoring of the lifestyle of the patient. In the following, the invention will be described in the context of the self-management of diabetes, in particular the self-management of insulin delivery and blood glucose measuring by the patient.

Figure 1:
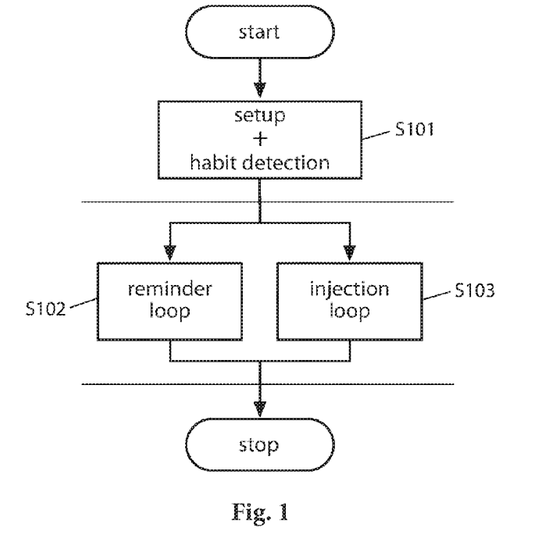
FIG. 1 shows a flow diagram of an embodiment of a process for generating reminders based on detected habits.

FIG. 1 shows a flow diagram of an embodiment of a process for generating reminders based on detected habits.

In an initial setup step S101, the patient related data and parameters are monitored and the patient's habits are determined based on the collected data. This habit detection is further used to set reminders for the patient. Subsequently, the process alerts the user about a missed insulin injection/bolus by executing a reminder loop (step S102). The process further executes an insulin loop (step S103) to alert the user in situations where the delivered dose of insulin does not correspond to the previously determined level.

Figure 2:
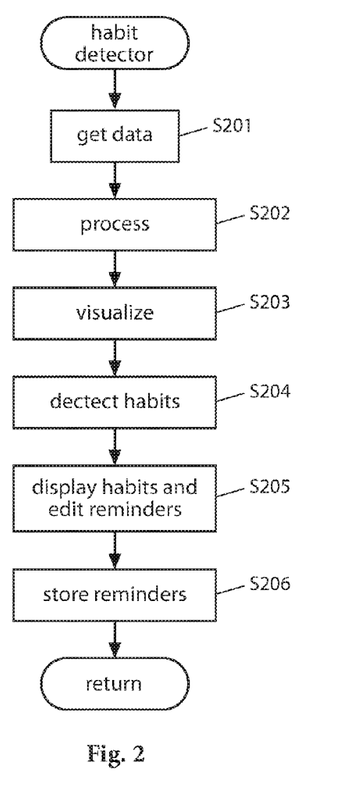
FIG. 2 shows a flow diagram of an embodiment of a process for detecting habits.

FIG. 2 shows a flow diagram of an embodiment of a process for detecting habits.

In order to monitor his/her lifestyle, a diabetic maintains a log of various parameters that are relevant and give an insight into his/her living habits and present state of health. For example, apart from recording blood glucose readings, insulin intakes etc., the amount of meals/carbohydrates consumed, exercise done/calories burnt etc may also be recorded. A combination of one or more of these parameters along with their analysis helps in detecting any unwanted deviation from what is expected for a healthy life.

This self-care i.e. self-monitoring of blood glucose makes a person responsible for his/her healthy living. It is desirable that method and systems that provide this functionality be as user friendly as possible because they have to be used by people coming from various educational backgrounds, technical understanding/friendliness, different age groups etc. The reports generated should not only provide a meaningful and detailed insight but also be easier to interpret.

The process of habit detection and reminder setup starts in step S201 by receiving the collected data. In some embodiments, the patient enters the collected data onto a self-management device. The self-management device may be a suitably configured Blood Glucose Monitor device of the kind similar to those known as such in the art. In other embodiments, the self-management device may be a separate device for entry of this data and its evaluation. Embodiments of self-management devices will be described in greater detail below. Furthermore, in some embodiments, the self-management device may automatically record at least some of the data without the need for a manual input. For example, if the device is an integrated blood glucose measuring device and self-management device, the time and/or the measured blood glucose level may directly be logged by the device for the purpose of subsequent habit detection. Similarly, if the device is an integrated insulin administration device and self-management device, the times of delivery and/or the doses of delivered insulin may be automatically logged for the purpose of subsequent habit detection. Preferably, the collected data corresponds to the user's actions over a period of several days, preferably weeks or even months, in order to provide a statistically representative sample.

Once the data has been entered, the raw data is processed (step S202), e.g. by determining distributions of different user actions over a modal day, as will be described in greater detail below.

Optionally, in step S203, the process presents the processed data to the user, e.g. by presenting one or more reports to the user, e.g. via a user interface of the self-management device, by printing one or more of the reports, or the like. For the ease of the user, these reports are preferably graphical.

In step S204, the process data is analyzed and any habits that are detectable from the data are identified. In some embodiments, the habit detection is performed fully automatic, while in other embodiments, the habit detection may involve different degrees of user interaction, e.g. by providing functionality that allows a user to point out habits in the presented reports.

In step S205, the process generates a set of reminders based on the detected habits. In one embodiment, the process displays the detected habits and proposed reminders corresponding to the detected habits to the user, and provides functionality that allows the user to edit the generated reminders, delete reminders, and add new reminders. Preferably, the habits and or reminders are presented via a graphical user interface.

In step 206, the generated and optionally edited reminders are stored in a memory of the device.

Figure 3:
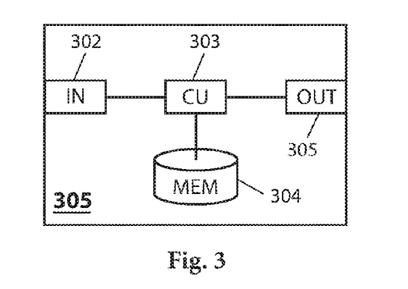
FIG. 3 shows a schematic block diagram of an embodiment of a user device for assisting a user in the self-management of a physiological condition.

FIG. 3 shows a schematic block diagram of an embodiment of a user device for assisting a user in the self-management of a physiological condition.

The device, generally designated 301, comprises a data input unit 302, a processing unit 303 configured to receive the data input via input unit 302, a memory 304 or other storage device connected to the processing unit 303, and an output unit 305 connected to the processing unit 302.

In some embodiments, the data input unit 302 comprises user input means such as push buttons, a keypad, a keyboard, a touch screen, a pointing device, e.g. a computer mouse, a stylus, a mouse pad, or the like, allowing a user to enter data, in particular the data to be recorded for the purpose of the habit detection. The input unit further allows the user to enter reminder parameters such as a type of reminder, a time or time interval. Alternatively or additionally, the input unit 302 may comprise different input means such as a data interface adapted to receive data from other devices, e.g. from a blood glucose measuring device, an insulin administration device, from a data processing device, or the like. The data interface may comprise any circuit or device suitable for data communication via a wired or a wireless channel. Examples of data interfaces include but are not limited to an infrared port, e.g. an IrDa port, a radio-frequency interface such as Bluetooth, a serial port, such as UBS, Fire-Wire, or the like. Alternatively or additionally, the input unit 302 may comprise an internal interface for receiving data from other components within the device 301, e.g. in an embodiment, where the device 301 comprises both a diabetes self-management device and a blood glucose measuring device and/or an insulin administration device.

The processing unit 303 may comprise a suitably programmed microprocessor or any other suitable processing means, such as Digital Signal Processors (DSP), Application Specific Integrated Circuits (ASIC), Programmable Logic Arrays (PLA), Field Programmable Gate Arrays (FPGA), special purpose electronic circuits, etc., or a combination thereof.

The memory 304 may be any suitable type of memory or storage device, such as a non-volatile memory, e.g. flash memory, EPROM, EEPROM, a hard disk, or the like.

The output unit 305 includes any suitable circuit or device for issuing a reminder, e.g. an audible reminder, such as a beep or other sound, a visual reminder, and/or a tactile reminder. Hence, the output unit may comprise a sound generator, a loudspeaker, an LED or other light source, a display such as and LCD display, a vibrator, etc., or any combination of the above.

In some embodiments, the output unit includes a display that provides a graphical user interface for presenting the results of the habit detection and/or reminder setup to the user and allowing the user to edit the detected habits and/or reminders as described herein. Alternatively or additionally, the output unit may comprise other output means such as a printer or printer port, a drive or port for receiving a storage medium, such as a memory card, a writable CD, a diskette, or the like.

The self-management device described herein may be a special-purpose medical device or a combined device providing self-management functionality as described herein in combination with an insulin administration device, a blood glucose measurement device or any other device used by a diabetes patient. In some embodiments, the device may be embodied as a suitably programmed general-purpose data processing device, such as a hand-held computer, a PDA, or the like, or a suitably configured/programmed personal communications device, such as a mobile telephone, or the like.

The self-management process described herein may be implemented by a single device as described above or by a system comprising more than one device. In particular, the data analysis including the habit detection and/or reminder setup can either be performed on the machine on which the data was entered, or the data can be transferred onto a general purpose computing device that can then perform the said functions.

The link up of these user device to another computing device such as a desktop, laptop, PDAs etc., allows an improved analysis of the data using the enhanced computational power available as well as sophisticated and specialized software designed for the purpose. Various statistical means may be employed to display the patient data for easy understanding as well as accurate and beneficial analysis. For instance, there can be a report which would show the patient's blood glucose level at various times of the day and indicate any undesired highs or lows. Similarly there can be a report for patient's food intake. These reports can be textual or various graphical representations such as bar graph, pie chart, histograms etc can be used to facilitate easier understanding of the results.

Modal day display is one such kind of display in which patient related events that occurred on different days are treated as if they occurred on a single day, thereby providing a compact overview of the patient's daily habitual patterns. Algorithms such as the 7 point algorithm may be used for such display. In this algorithm the display is before and after each main meal i.e. breakfast, lunch and dinner and at sleep time.

Figure 4:
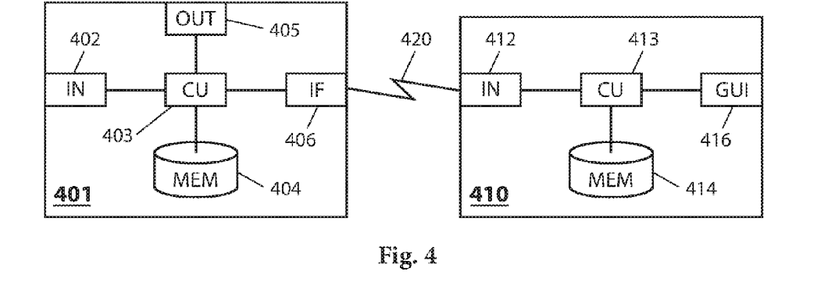
FIG. 4 shows a schematic block diagram of an embodiment of a system for assisting a user in the self-management of a physiological condition.

FIG. 4 shows a schematic block diagram of an embodiment of a system for assisting a user in the self-management of a physiological condition.

The system comprises a user device, e.g. a suitably configured drug administration device, generally designated 401, comprising an input unit 402, a processing unit 403, a memory 404, and an output unit. The user device 401 and the above-mentioned components correspond to the user device 301 and its corresponding components described in connection with FIG. 3 and will therefore not be described again here.

The user device 401 further comprises an interface unit 406 adapted to communicate data with an external data processing system 410. To this end, the data processing system 410 comprises a corresponding interface unit 412. Each of the interface units 406 and 410 may include any suitable circuit or device adapted to provide data communication between the user device 401 and the data processing system 410. Examples of interface units include but are not limited to an infrared port, e.g. an IrDa port, a radio-frequency interface such as Bluetooth, a serial port, such as UBS, FireWire, or the like, a local area network (LAN) connection, a wireless local area network (WLAN) connection, an ADSL connection, an IDSN connection or any other Internet connection, a data connection via a cellular telecommunications network, e.g. via GSM, GPRS, UMTS, or the like. In yet alternative embodiments, data may transferred between the user device 401 and the data processing system 410 by means of a data carrier, such as a memory stick, a diskette, a smart card, or the like.

The data processing system 410 further comprises a processing unit 413, a memory or other storage device 414, e.g. as described in connection with the processing unit 303 and the memory 304. Furthermore, the data processing system 410 provides a graphical user interface 416, e.g. via a suitable display and a corresponding input device, such as a keyboard, keypad, pointing device, etc. For example, the data processing system 410 may be a suitably programmed conventional computer, e.g. a desktop personal computer (PC), a portable computer, or the like.

Hence, in the embodiment of FIG. 4, the data entry may be performed via the user device 401 and/or the data processing system 410. The recorded data is then communicated to the data processing system 410, where the data processing, habit detection, and the graphical presentation and editing of the resulting reminders and optionally data analysis results are performed. The generated reminder data items are then transferred back to the user device. Hence, in this embodiment, the habit detection and setup of the user device is performed at the data processing system 410, thereby reducing the requirements for the user device in terms of processing power and usability of the user interface.

This arrangement between the user device and the data processing system may be a simple one-to-one link between the two entities. However, they may also be part of a patient-doctor-relative-peer network. For example the data processing system may periodically logon to a Local Area Network or Internet, or the like, to transmit the user readings to a remote database server that might be used to generate reports from a different computing system such as that of a doctor, relative of the patient and the like. These computing devices can be general-purpose desktops or other variations such as laptop, cell phones, PDAs etc.

As described herein, the aforementioned system can be used for 1) visualization, 2) detection, 3) evaluation, 4) entry of a diabetic's habits and 5) setting up a mobile dosing device via a wireless transmission. The system can visualize a diabetic's historical data in such a way as to emphasize temporal habits regarding insulin dosing, food consumption, blood glucose measurements and exercise. The system may also determine the strongest habits and make this information available to the user (diabetic or health care professional (HCP)). Detected habits can be transferred, e.g. wirelessly, to a mobile dosing device. The system may also provide the ability for the user (diabetic or HCP) to modify future habits by setting up reminders for the diabetic.

Habit detection can be done using various statistical and logical models. In the following different embodiments of automatic habit detection processes will be described with reference to FIGS. 5-7.

Figure 5:
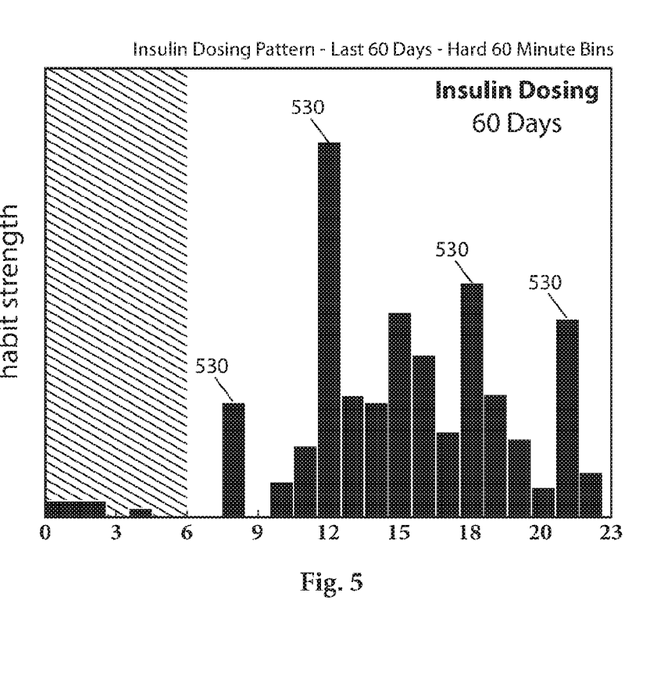
FIG. 5 illustrates an embodiment of a habit detection process.
Figure 6:
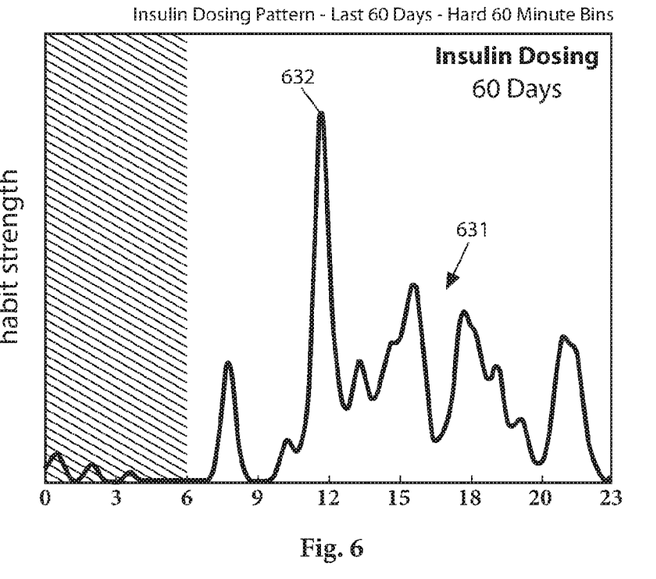
FIG. 6 illustrates another embodiment of a habit detection process.

In particular, FIGS. 5 and 6 illustrate two embodiments of methods for detecting temporal habits of insulin injections. Both embodiments take as input a set of recorded times of day at which the user has performed an insulin injection, e.g. data recorded over a predetermined number of days. It is understood that the methods may also be applied to the detection of other temporal habits, such as the times of blood glucose measurements. The method may also be applied to the detection of habits that are dependant on a variable other than time of day.

FIG. 5 shows a histogram chart of insulin injections over a modal day, where the data is based on recordings taken over a period of 60 days. Each bar of the histogram chart illustrates the number of insulin dosages delivered within a corresponding 1 h window during a modal day. As can be easily observed, the habits are clearly visible around breakfast, lunch, dinner and somewhat near bedtime as indicated by reference numeral 530.

Hence, the strongest habits may automatically be detected by a sliding window process: A sliding window, i.e. a time interval of a predetermined width, e.g. 1 hour, is moved across the modal day, all events falling inside the window are counted and the interval with most events represents the strongest habit, these events are then excluded from the next count, which finds the second strongest habit, etc.

FIG. 6 shows a chart based on the same data as in FIG. 5. In this embodiment, each insulin delivery event is represented by a normal distribution centred around the recorded time of delivery and having a predetermined width, e.g. such that 95% of the area under the distribution falls within a 60 minutes window. The total distribution 631 is then obtained as a superposition/summation over all individual distributions. The strongest habits correspond to the heighest local maxima of the distribution. For example, the strongest habit corresponds to the local maximum 632.

Hence, the strongest habits may be detected by a Gaussian smearing process, wherein a normal distribution of a predetermined width is assigned to every event, and wherein the individual normal distributions are summed in a modal day and local maxima are used as habit markers. It is understood that the superposition can be performed in a variety of ways and a variety of smearing functions may be used instead of a normal/Gaussian distribution.

Figure 7A:
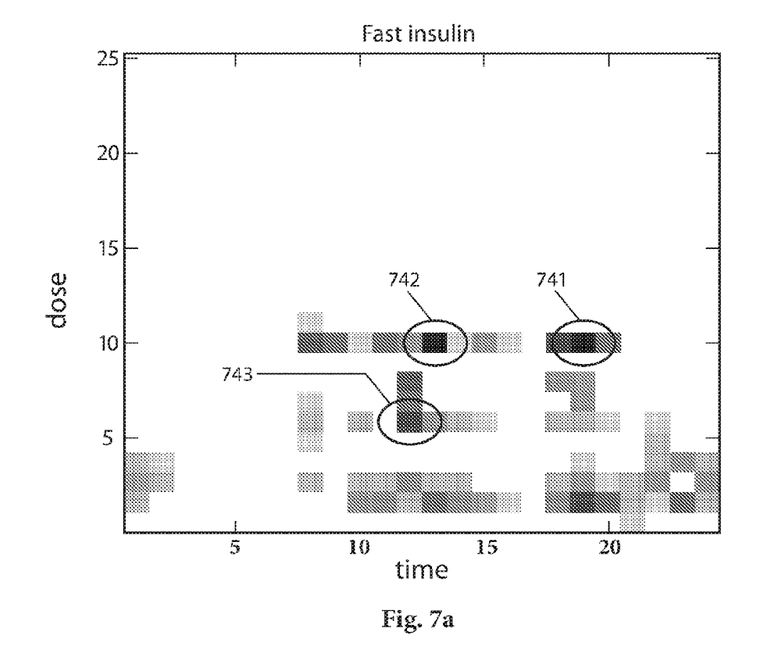
FIG. 7a shows a histogram for fast insulin.
Figure 7B:
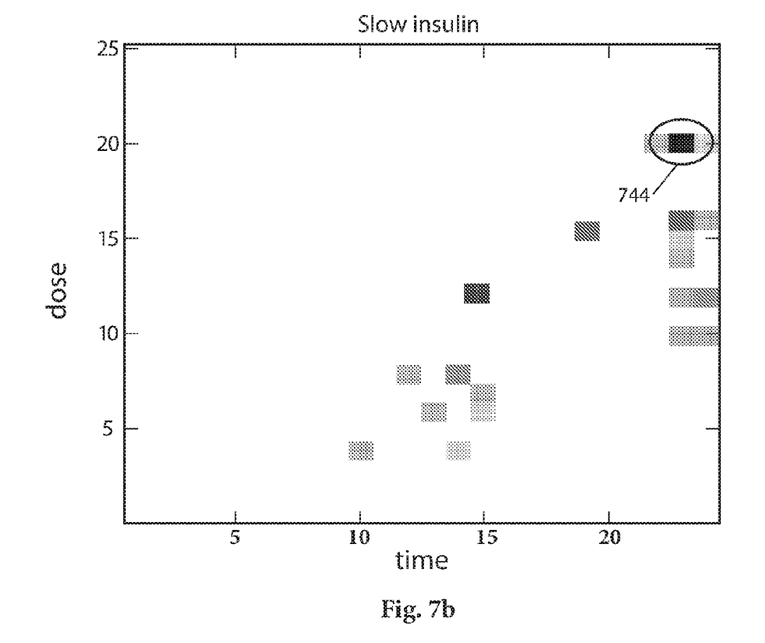
FIG. 7b shows a histogram for slow insulin.
Figure 7C:
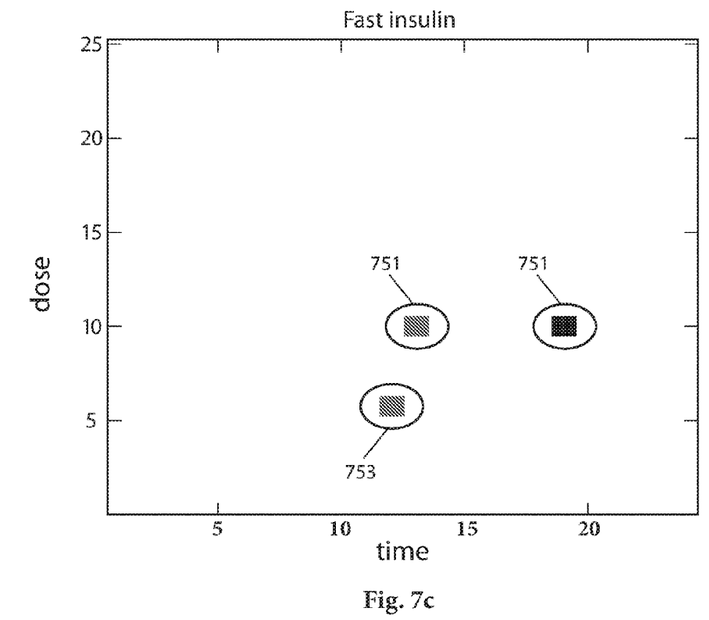

FIGS. 7a-c show grey-scale coded two dimensional histogram charts. The abscissa of each chart corresponds to the time of day of a modal day, while the ordinate corresponds to insulin doses. In FIGS. 7a-b, each grey-scale square corresponds to the number of events from a series of user recorded events falling within the corresponding time and dose intervals. Different grey scales correspond to different numbers/counts, i.e. correspond to different heights of the histogram. While FIG. 7a shows the histogram for fast insulin, FIG. 7b shows the corresponding histogram for slow insulin.

In FIG. 7a, the strongest peaks are marked by reference signs 741, 742, and 743. In FIG. 7b, the strongest peak is marked by reference sign 744.

The strongest habits with respect to insulin administration times and doses may be detected by the following process: First a data representation of a two dimensional histogram as shown in FIGS. 7a-b is generated. To this end, a rectangular window/bin of predetermined width, e.g. 1 hour, and a predetermined height, e.g. 1 International Unit (IU) insulin, is moved across the modal day in steps corresponding to the predetermined width and heights of the rectangular window/bin. All events falling inside the window are counted. In order to detect the strongest habits, the events with the highest count may be determined as the strongest habit. In one embodiment, the strongest habit may be automatically detected by an area integration technique over the above two-dimensional histogram: The distribution modelled by the above two-dimensional histogram is integrated over, and the smallest possible area that represents a given number of injections (e.g. 20%) is determined. The area is represented by a number of two-dimensional bins. The time and dose coordinates of the thus detected bins are selected as the strongest habits.

In an alternative embodiment, a smearing operation and subsequent superposition of smeared distribution functions as described above may be performed in two dimensions.

It is further understood that user actions that depend on different pairs of parameters may be processed in a similar way.

Figure 7D:
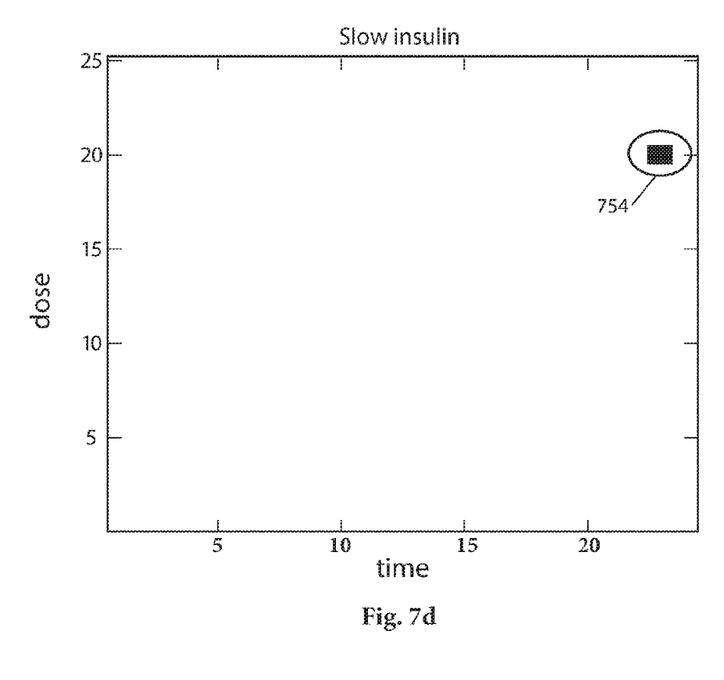
FIG. 7d shows the only detected habit for slow insulin of FIG. 7b.

FIGS. 7c-d show the strongest habits detected by the above process for the fast and slow insulin histograms of FIGS. 7a-b, respectively. In the case of fast insulin, FIG. 7c shows the three detected habits designated 751, 752, and 753. In the case of slow insulin, FIG. 7d shows the only detected habit designated 754.

In the above, three examples of automatic habit detection processes that have been found useful were described. Hence, the system described herein provides a habit detector function, which is able to detect meal time, time for BG measurements, injection time and/or injection doses.

Preferably the output of the habit detector is used as default values for the setup of reminders and dose warnings where the reminders may be manually edited/modified by the user or HCP. Hence, the user can use the habit-based reminder function as a warning tool when he deviates from a normal or desired treatment pattern or behaviour. This way the function will be able to decrease the number of missing injections and wrong insulin doses significantly and thereby improve the overall diabetes management.

It is understood that the habit detection may also be performed interactively, i.e. allowing a user to control the detection. For example, the recorded historical data may be visualised on a graphical user interface. For example, the data may be visualised as a modal day histogram or similar view, e.g. as graphs shown in any of FIGS. 5-7. The habits may then be manually detected by the diabetic or HCP based on the visualization, or habits may be detected by the system and presented to the diabetic or HCP for review.

Once detected, the habits may be evaluated by the diabetic, HCP or the system, e.g. based on best practice rules for a lifestyle, eating habits, etc. The detected habits may be translated into reminders. Alternatively, the reminders may be edited by the diabetic, HPC, or the system based on the above evaluation of the detected habits. Hence, the diabetic may be encouraged to change his/her habits in the future.

The modification of habits based on the detected habits may be illustrated by the following example: The user tends to forget the morning insulin due to busy mornings with lots of things to attend. The system described herein detects that the morning insulin typically is taken between 7 and 11 a.m. and a reminder is given if the insulin has not been injected by 11 a.m. This is the actual habit—but not one the user wants to retain. The user can set the reminder to 8 a.m. and a beep will sound once e.g. every 5 minutes until the insulin has been injected. If the system can remind the diabetic about the missing injection e.g. 5 times a month the result can potential be a decrease in the HbA1c around 0.20% points.

In the following, examples of graphical user interfaces for the user-friendly visualisation and/or editing of detected habits and reminders will be described in connection with FIGS. 8-10.

Figure 8:
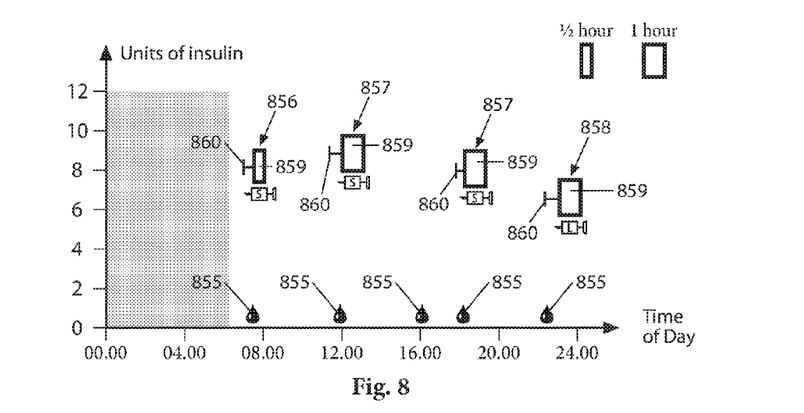
FIG. 8 illustrates an embodiment of a graphical user interface for visualizing the results of the habit detection.

FIG. 8 illustrates an embodiment of a graphical user interface for visualizing the results of the habit detection. The drop-shaped symbols 855 show the time of day for the strongest blood glucose measurement habits, i.e. the times when the user usually measures the blood glucose level. The symbols 856, 857, and 858 including a needle icon show the time and doses for the strongest insulin injection habits. The abscissa of the location of each of the symbols 856, 857, and 858 illustrate the respective time of day, while the ordinate of the location of each of the symbols 856, 857, and 858 illustrate the respective insulin dose. The needle symbols further illustrate the type of insulin administered at the respective times of the day: The symbols 856 and 857 correspond to fast insulin, while symbol 858 illustrates slow insulin. Each of the symbols 856, 857, and 858 illustrate a habit interval and a reminder interval. In particular, each symbol includes a rectangular box 859 that indicates the time interval of a detected habit and a line 860 indicating the respective start time of the corresponding reminder time interval. The widths of the boxes 859 indicate the extent to which the detected habit was localised in time, i.e. a resolution of the detected habit. In the example of FIG. 8, the boxes 859 indicate whether a habit was localized within ½ hour or within 1 hour, i.e. how accurately/consistent the user has followed the corresponding habit. In one embodiment, the width of the box 859 is determined from the width of the corresponding peak in a histogram as described in connection with FIG. 5 or 6, or from the number of bins of the detected areas in a histogram as described in connection with FIG. 7. It is understood that the detectable smallest resolution is related to the width of the windows/bins and/or the amount of smearing in the habit detection methods described herein. In FIG. 8, the vertical lines 860 and the right edges of the boxes 859 define the respective start and finish times of the reminder intervals of the corresponding reminder data items.

Figure 9:
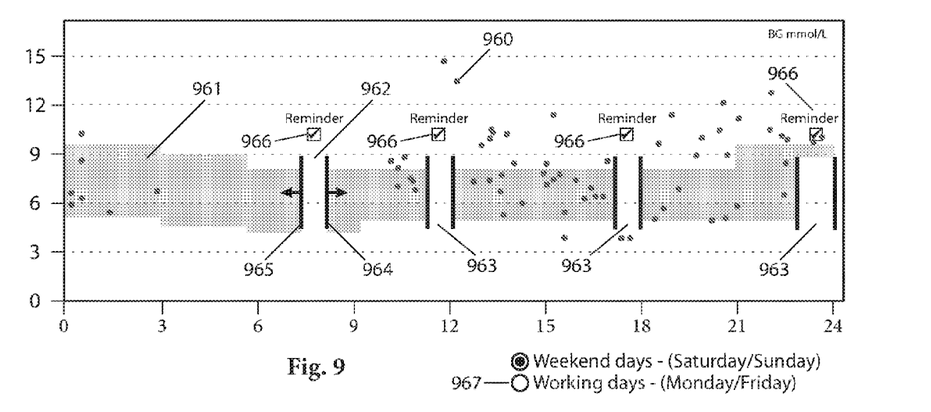
FIG. 9 illustrates an embodiment of a graphical user interface for visualizing and editing reminder data items.

FIG. 9 illustrates an embodiment of a graphical user interface for visualizing and editing reminder data items. The user interface shows a graph where the abscissa corresponds to the time of day and the ordinate to measured blood glucose levels. The graph shows historic data as dots, e.g. dot 960. Each dot corresponds to a previously recorded measured data, i.e. to a measured blood glucose level at a given time of day. The differentiated target blood glucose levels at the different times of the day are indicated as a grey band 961. Based on detected habits and a subsequent evaluation of the habits, the desired future times for blood glucose measurements are set as intervals 962 and 963, each illustrating a time interval during which the patient should measure the blood glucose level. Each interval further has an associated check box 966 associated with it, i.e. an active component of the user interface that can be activated by the user by clicking at the check box with a pointing device or the like. When a checkbox is checked, the corresponding interval is setup as an active reminder, i.e. the time interval is stored as part of a reminder data item an marked as active. The limits of each interval, e.g. limits 964 and 965 of interval 962, are also active components of the user interface that may be moved along the abscissa, e.g. by a drag and drop operation with a pointing device, thereby allowing a user to change the start and stop time of the time interval. It is understood that other means for inputting parameters of the reminders may be used, such as other graphical input means, e.g. sliders, selection boxes, etc. or dialog boxes that allow the times to be input via a keyboard. The user interface of FIG. 9 further allows setting up different reminders for weekdays and for weekends/holidays, by selecting a weekday view or a weekend view, via selection radio buttons 967.

Figure 10:
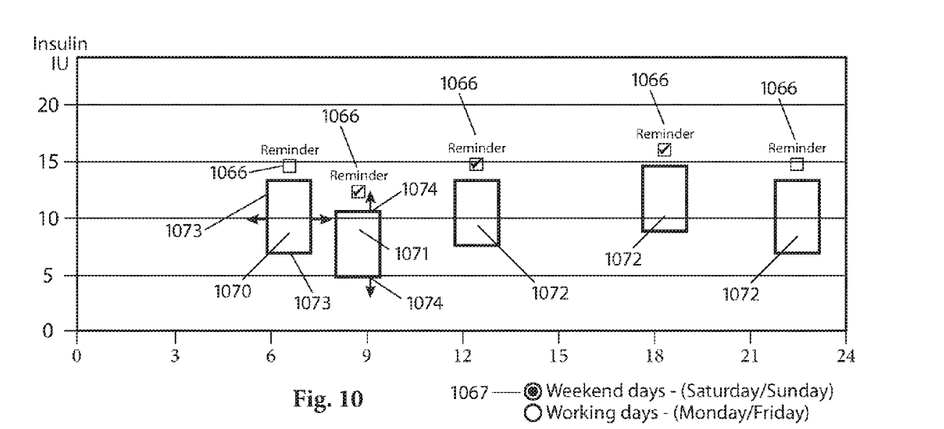
FIG. 10 illustrates another embodiment of a graphical user interface for visualizing and editing reminder data items.

FIG. 10 illustrates another embodiment of a graphical user interface for visualizing and editing reminder data items. The user interface shows a graph where the abscissa corresponds to the time of day and the ordinate to measured blood glucose levels. The user interface further shows a number of graphical area objects 1070, 1071, and 1072, each representing a habit data item generated based on a detected insulin administration habit, e.g. as detected by the habit detection process described in connection with FIG. 7. Each area object corresponds to a time interval corresponding to the width of the object, i.e. the size in the direction of the abscissa. Each area object further corresponds to a dose interval corresponding to the height of the object, i.e. the size in the direction of the ordinate. Furthermore, each area object may indicate a type of insulin, e.g. by means of different shadings, background colors, or other visual indication. Furthermore, each area object has a check box 1066 associated to it as described above. The check box of a habit data item causes, when checked, the setup of an active reminder data item corresponding to the time and dose intervals of the habit data item. The vertical lines of each area object, exemplified by lines 1073 of object 1070, are active components of the user interface that may be moved along the abscissa, e.g. by a drag and drop operation with a pointing device, as described above, thereby allowing a user to change the start and stop time of the time interval. Similarly, the horizontal lines of each area object, exemplified by lines 1074 of object 1071, are active components of the user interface that may be moved along the ordinate, thereby allowing a user to change the dose interval associated with a reminder data item. The user interface of FIG. 10 further allows setting up different reminders for weekdays and for weekends/holidays, by selecting a weekday view or a weekend view, via selection radio buttons 1067.

Hence, in the above, different user interfaces for the visualization and evaluation of habits and for the setup of reminders have been described. When the habit detection/evaluation is performed on a separate computer, the detected habits can be transferred, e.g. wirelessly, to a mobile dosing device and used to modify future habits by setting up reminders for the diabetic.

It is understood that a system, e.g. an insulin administration device, as described herein may also include basic warnings and reminder functions without any prior habit detection, alerting a user about forgotten insulin injections, if the insulin dose is outside the normal range, or in case of other events of forgotten actions. For example, default values for the injection time slots and the dose limits may be factory set in the production of the device. Hence, the basic reminder functions do not perform any statistics on the user's data, but it offers a possibility of setting reminders and warnings on missing or unusual actions. If no insulin dose is taken during some specific time slot, then a reminder sounds at the end of a preset time slot. Furthermore a dose interval can be related to each meal. If a dose outside that interval is dialled a warning is sounded.

It is understood that, for all reminders, additional settings may be made by a user. For example, the user may enter a snooze interval for time related reminders. If the snooze interval is 0, the reminder keeps ringing until action is taken. If set to 5 minutes it beeps once every 5 minutes until the insulin has been injected.

The above user interfaces my be part of a setup menu for setting the functions of a user device as described herein. In one embodiment, the setup menu allows the setting up of general reminders/general purpose reminders, i.e. reminders at predetermined times t that cause the display of a predetermined text, e.g. "pick up kids". Hence, a general reminder data item includes a tuple (t, "text").

The setup menu further allows the setting up of the start times $t_{s,x}$ and end times $t_{e,x}$ of a number $N_x$ of injection intervals, i.e. x=1, . . . , $N_x$. A typical choice is $N_x$=4, corresponding to injections in the morning, at lunch, at dinner, and at bedtime. Similarly, the setup may include menus for setting up the insulin dose intervals, time intervals for glucose level measurements, mealtimes to avoid low blood glucose levels, and/or the like. A reminder data item for an insulin administration may thus comprise a time interval, a dose interval, and an activation flag indicating whether the reminder is activated. Furthermore, the setup menu allows the setting up of a snooze function, e.g. by specifying a snooze interval.

The setup menu further allows the running of a habit detector as described herein in order to generate suggestions for the above reminders. Furthermore, the setup menu allows the activation and deactivation of certain types of reminders, e.g. general reminders, mealtime reminders, glucose measurement reminders, insulin administration reminders, etc. In some embodiments, the device may provide functionality for synchronising the reminders with other computerised calendar or workflow systems.

Hence, the user device integrates a number of different reminders in a single device in a user-friendly and consistent way.

Furthermore, the device may comprise functionality allowing a reminder or an alarm in the case that an injection has been missed for a long period of time to be issued to an external recipient, e.g. by initiating a voice call, by sending an SMS, an email, or the like. Accordingly, the setup menu may comprise functionality for setting up these types of functions including a telephone number to call/send a message to, etc.

In the following, and embodiment of the reminder loop and the insulin loop described in connection with FIG. 1 will be described in more detail.

Figure 11:
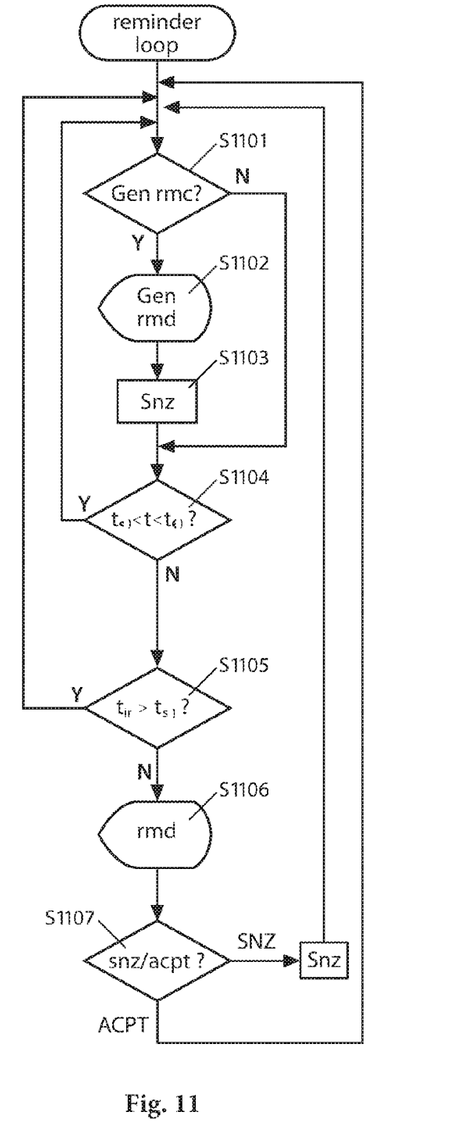
FIG. 11 shows a flow diagram of a reminder loop for issuing reminders about forgotten insulin administration.

FIG. 11 shows a flow diagram of a reminder loop for issuing reminders about forgotten insulin administration. The process receives the system time of the user device as an input which is assumed to correspond to the actual time at the location of the user.

In an initial step S1101, the process compares the reminder times of the general reminders set in the system to the system time. If the system time has reached the time of a general reminder, the process proceeds at step S1102. Otherwise, the process proceeds at step S1104. At step S1102, the process issues a reminder via the user interface of the user device, e.g. by displaying a text associated with the general reminder and/or by beeping, vibrating, flashing, or the like.

The process proceeds at step S1103, where a snooze function is activated, i.e. the reminder is set to reissue after a predetermined snooze interval. If no snooze interval is set, the alarm may continue until acknowledged by the user.

At step S1104, the process determines whether the system time lies within the time interval of any of the set insulin alarms, i.e. whether $t_{s,x}<t<t_{e,x}$, for any x=1, . . . , $N_x$. If yes, the process returns to step S1101; otherwise, the process proceeds at step S1105.

In step S1105, the process determines whether the time of the last insulin administration $t_{in}$ lies after the start of the most recent reminder time interval x'. If yes, i.e. if $t_{in}>t_{s,x'}$, the process returns to step S1101, because in this case an insulin administration has been performed within the set time limit, and no reminder is needed, thereby avoiding unnecessary reminders. The time $t_{in}$ may be input by the user or registered by the device, e.g. by a parallel running insulin process as described below. For example, the user may push a predetermined button of the device to indicate that the user has administered insulin or, if the device is integrated with an insulin administration device, the time of administration may be automatically registered by the device. If the test in step S1105 is negative, i.e. $t_{in} \le t_{s,x'}$, the process proceeds at step S1106 by issuing a reminder, because in this case no insulin was administered during the relevant time interval.

In step S1106, a reminder is issued, e.g. by displaying a predetermined message, by sounding a beep, by vibrating or any other suitable audible, visual, and/or tactile means. The user may acknowledge the alarm or activate a snooze function (step S1107). If the user acknowledges the reminder the process returns to step S1101; otherwise the process activates a snooze function (step S1108) as described above and returns to step S1101.

Figure 12:
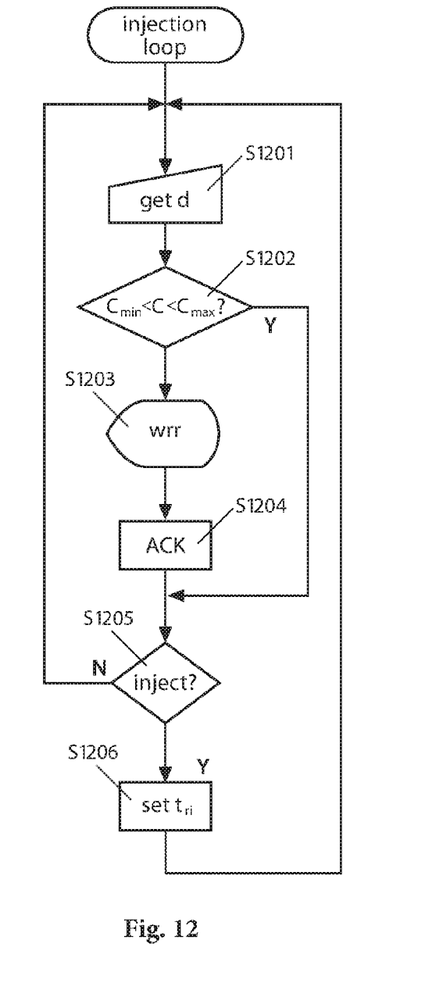
FIG. 12 shows a flow diagram of an insulin loop for issuing reminders about insulin doses that lie outside a predetermined interval.

FIG. 12 shows a flow diagram of an insulin loop for issuing reminders about insulin doses that lie outside a predetermined interval. The process is triggered by the receipt of a dose indication d (step S1201), e.g. by the user entering a dose administered/to be administered, or by the device receiving a dose information directly from an insulin administration device or an internal insulin administration module of a combined device.

In subsequent step S1202, the process determines whether the received dose d lies within the dose interval for the insulin reminder data item that is due at the present time (based on the time interval of the reminder data item). If the dose is outside the preset limits, the process proceeds at step S103 and issues an alarm/reminder as described above, e.g. by displaying an appropriate message and/or by other audible, visual, and/or tactile means. Otherwise, the process continues at step S1205. From step S1203, the process proceeds at step S104 awaiting the user to acknowledge the alarm. When the user acknowledges the alarm, the process continues at step S1205.

In step S105, the process determines whether the user performs an insulin administration, e.g. by receiving a corresponding indication from the user, or directly from the insulin administration device/module. If no insulin is administered, the process returns to step S1201 and awaits a new dose indication. Otherwise, the process updates the time $t_{in}$ of the last insulin injection with the current time (step S1206) and returns to step S1201.

Although some embodiments have been described and shown in detail and using diabetes as a central theme, the invention is not restricted to them, but may also be embodied in other ways within the scope of the subject matter defined in the following claims. The invention may also be applied to other similar applications including but not restricted to general health monitoring, the self-treatment of asthma, the administration of blood coagulation medicine, the administration of growth hormone, etc.

The method, product means, and device described herein can be implemented by means of hardware comprising several distinct elements, and by means of a suitably programmed microprocessor. In particular, the features of the method described herein may be implemented in software and carried out on a data processing device or other processing means caused by the execution of program code means such as computer-executable instructions.

The executing steps can be realized in a centralized fashion in one computer system, or in a distributed fashion where different elements are spread across several interconnected computer systems. Computer program means or computer program in the present context mean any expression, in any language, code or notation, of a set of instructions intended to cause a system having an information processing capability to perform a particular function either directly or after either or both of the following: a) conversion to another language, code or notation or b) reproduction in a different material form.

In some instances, the program may be supplied to the user encoded on a CD-ROM or a floppy disk or read by the user from the network via a modem device connected to the computer. Still further, the computer system can load the software from other computer readable media. This may include magnetic tape, a ROM or integrated circuit, a magneto-optical disk, a radio or infra-red transmission channel between the computer and another device, a computer readable card such as a PCMCIA card, and the Internet and Intranets including email transmissions and information recorded on Internet sites and the like. The foregoing are merely examples of relevant computer readable media. Other computer readable media may be practiced without departing from the scope and spirit of the invention. In the device claims enumerating several means, several of these means can be embodied by one and the same item of hardware, e.g. a suitably programmed microprocessor, one or more digital signal processor, or the like. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A method of assisting a user in the self-management of diabetes, the method comprising
    obtaining data about occurrences of at least a first type of user actions;
    detecting a user habit from the obtained data; and
    generating a reminder data item from the detected user habit, and
    storing the generated reminder data item in a device to be carried by the user said device is one of a blood glucose measuring device and an insulin administration device,
    wherein detecting a user habit comprises determining a distribution of occurrences of said first type of user actions over a predetermined period of time and detecting a time interval during which said first type of user actions typically occurs.

2. A method according to claim 1, wherein the reminder data item comprises a time interval during which the user action is to be performed.

3. A method according to claim 1, wherein the user action comprises one of a blood glucose measurement, a meal intake, physical exercise, and a medication.

4. A method according to claim 1, wherein detecting the user habit includes graphically presenting a representation of the obtained data.

5. A method according to claim 4, wherein said graphical representation includes at least one of a histogram, a line graph and a bar graph.

6. A method according to claim 1, wherein detecting a user habit further comprises at least one of a sliding window operation, a Gaussian smearing, and an area integration of the determined distribution.

7. A method according to claim 1, wherein the first type of user action includes an intake of a medicament, and wherein detecting the user habit/habitual pattern includes detecting a typical dose interval of the medicament.

8. A method according to claim 7, wherein detecting the user habit comprises
    determining a time of day and a dose of each medication intake;
    determining respective numbers of medication intakes within a plurality of time intervals and with a dose within a predetermined dose interval to obtain a distribution of medication intakes as function of time of day and of dose; and
    determining a combination of a time interval and a dose interval as a maximum of said distribution.

9. A method according to claim 7 wherein reminder data item comprises a time constraint and a dose constraint for a medication to be taken by a user; and wherein the method further comprises
    receiving an indication of a medication event, if any, said indication comprising time and dose information about a medication taken by the user;
    issuing a reminder if no indication about at least one medication event complying with both the time constraint and the dose constraint of the reminder data item is received.

10. A method according claim 1, wherein generating a reminder data item comprises
    presenting at least one suggested parameter of the reminder data item to the user; and
    providing editing means allowing the user to edit the suggested parameter.

11. A method according to claim 1, wherein detecting the user habit comprises
    determining a time of day of each of the occurrences of the first type of user actions;
    determining respective numbers of said occurrences within a plurality of time intervals; and
    determining one of said time intervals as corresponding to a largest number of occurrences.

12. A method according to claim 1, wherein detecting the user habit comprises
    determining a time of day of each of the occurrences of the first type of user actions;
    generating a predetermined distribution function around each occurrence;
    combining the generated distribution functions to obtain a combined distribution functions; and
    determine a user habit as a maximum of the combined distribution function.

13. A method according to claim 12, wherein the predetermined distribution function is a Gaussian distribution function.

14. A method according to claim 1, wherein the reminder data item comprises a time interval of a modal day during which a user should take an action of the first type; and wherein the method further comprises
    receiving an indication when a user action of the first type has occurred;
    issuing a reminder if no indication about an occurred user action has been received within said time interval.

* * * * *

UNITED STATES PATENT AND TRADEMARK OFFICE
CERTIFICATE OF CORRECTION

PATENT NO.        : 9,501,949 B2                                    Page 1 of 1
APPLICATION NO.   : 11/664561
DATED             : November 22, 2016
INVENTOR(S)       : Hansen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2991 days.

Signed and Sealed this

Twenty-fifth Day of September, 2018

Andrei Iancu
*Director of the United States Patent and Trademark Office*